United States Patent
Xie et al.

(10) Patent No.: US 12,176,074 B2
(45) Date of Patent: Dec. 24, 2024

(54) COMPOUND FUNCTION PREDICTION METHOD BASED ON NEURAL NETWORK AND CONNECTIVITY MAP ALGORITHM

(71) Applicants: BEIJING GIGACEUTICALS TECH. CO. LTD, Beijing (CN); PEKING UNIVERSITY, Beijing (CN)

(72) Inventors: Zhengwei Xie, Beijing (CN); Jie Zhu, Beijing (CN); Jingxiang Wang, Beijing (CN); Mingjing Gao, Beijing (CN); Zhurui Liu, Beijing (CN)

(73) Assignees: BEIJING GIGACEUTICALS TECH. CO. LTD, Beijing (CN); PEKING UNIVERSITY, Beijing (CN)

( * ) Notice: Subject to any disclaimer, the term of this patent is extended or adjusted under 35 U.S.C. 154(b) by 0 days.

(21) Appl. No.: 18/278,411

(22) PCT Filed: Apr. 25, 2021

(86) PCT No.: PCT/CN2021/089686
§ 371 (c)(1),
(2) Date: Aug. 23, 2023

(87) PCT Pub. No.: WO2022/178961
PCT Pub. Date: Sep. 1, 2022

(65) Prior Publication Data
US 2024/0136025 A1   Apr. 25, 2024
US 2024/0233878 A9   Jul. 11, 2024

(30) Foreign Application Priority Data
Feb. 23, 2021 (CN) .......................... 202110199635.9

(51) Int. Cl.
*G16C 20/30* (2019.01)
*G16C 20/10* (2019.01)
(Continued)

(52) U.S. Cl.
CPC ............. *G16C 20/30* (2019.02); *G16C 20/10* (2019.02); *G16C 20/70* (2019.02); *G16C 20/90* (2019.02)

(58) Field of Classification Search
CPC ........ G16C 20/30; G16C 20/10; G16C 20/70; G16C 20/90
See application file for complete search history.

(56) References Cited

U.S. PATENT DOCUMENTS

2020/0365270 A1    11/2020  Kazemi Oskooei et al.
2021/0090694 A1*   3/2021   Colley ................... G16H 15/00
(Continued)

FOREIGN PATENT DOCUMENTS

CN     110517790     11/2019
CN     110876751     3/2020
(Continued)

OTHER PUBLICATIONS

"International Search Report (Form PCT/ISA/210) of PCT/CN2021/089686," mailed on Nov. 23, 2021, with English translation thereof, pp. 1-4.

*Primary Examiner* — Tung S Lau
(74) *Attorney, Agent, or Firm* — JCIPRNET (57) ABSTRACT

The present disclosure provides a compound function prediction method based on a neural network and a connectivity map (CMAP) algorithm. The compound function prediction method is used to predict an efficacy of a compound, and the compound function prediction method includes the following steps: constructing a compound molecule-encoding vector neural network; constructing and training an encoding vector-marker gene expression variation deep neural network; constructing and training a marker gene expression level or gene expression variation-whole genome gene expression level or gene expression variation neural network; constructing upregulated and downregulated gene sets (Continued)

of a disease or a phenotype; and evaluating a correlation between the compound and the disease or the phenotype.

8 Claims, 5 Drawing Sheets

(51) Int. Cl.
*G16C 20/70* (2019.01)
*G16C 20/90* (2019.01)

(56) References Cited

U.S. PATENT DOCUMENTS

| | | | | |
|---|---|---|---|---|
| 2021/0142173 | A1* | 5/2021 | Cheng | G06N 3/08 |
| 2022/0130493 | A1* | 4/2022 | Turner | G16C 20/90 |
| 2023/0038256 | A1* | 2/2023 | Tal | G16B 40/00 |

FOREIGN PATENT DOCUMENTS

| | | |
|---|---|---|
| CN | 111297882 | 6/2020 |
| CN | 111785326 | 10/2020 |
| CN | 112216396 | 1/2021 |
| CN | 112289369 | 1/2021 |

\* cited by examiner

Correlation coefficient r between experimental vector and predicted vector in training set

# COMPOUND FUNCTION PREDICTION METHOD BASED ON NEURAL NETWORK AND CONNECTIVITY MAP ALGORITHM

CROSS-REFERENCE TO RELATED APPLICATION

This application is a 371 of international application of PCT application serial no. PCT/CN2021/089686, filed on Apr. 25, 2021, which claims the priority benefit of China application no. 202110199635.9, filed on Feb. 23, 2021. The entirety of the above-mentioned patent application is hereby incorporated by reference herein and made a part of this specification.

1. TECHNICAL FIELD

The present disclosure relates to pharmacy informatics and artificial intelligence, and in particular to a drug function evaluation method based on a neural network and a gene set enrichment analysis (GSEA) algorithm.

2. BACKGROUND ART

According to statistics, it takes 10 to 14 years and over $200 million for each new drug to be developed, tested, and marketed. Speeding up the development and testing of new drugs has always been the key and difficult point in speeding up the drug development stage. In recent years, due to the development of disciplines such as biochemistry and physiological pathology, new methods have emerged for drug screening, and some molecular cell level drug screening models have emerged. In addition, with the development of more advanced detection technology, automation technology, and computer technology, high-throughput screening (HTS) technology emerged in the late 1990s. HTS mainly relies on automated operating systems implemented by laboratory robots and highly sensitive detection processes, and includes approaches such as spectrophotometry and fluorescence detection technology. The emergence of HTS has greatly accelerated the speed of drug screening, but it still has significant limitations, including high cost, difficulty in model construction, and limited number of models. In China, due to the late development of the drug screening system, only a few national key laboratories have HTS systems. Laboratory robots are difficult to be popularized due to their high cost, and various detection methods still cannot be separated from manual statistics and analysis.

In recent years, with the rapid development of computer technology, the screening and development of new drugs have gradually been combined with computer technology. In the existing research, computer technology is mostly used for statistical processing of experimental data and analysis and classification of existing features, and is further used in computer-aided drug design. In recent years, there have been some studies applying machine learning to improve the effectiveness of virtual screening. Indeed, virtual screening plays an important role in drug screening, but it still relies on existing small molecule databases and various artificially classified features, insufficient to reflect the actual use effect of drugs. Research institutions and laboratories need a drug screening system that can be applied to evaluate drug efficacy in practice. The drug screening system is expected to have high accuracy, strong anti-interference ability, short time, and to overcome the constraints of existing databases, artificially classified features, and high-cost laboratory robots.

In summary, the existing drug screening systems cannot meet the growing scientific research needs. Therefore, it is necessary to establish a simple, efficient, accurate, and low-cost HTS system. Machine learning methods can be applied to the establishment of laboratory drug screening systems. As a branch of machine learning, deep learning originated from the study of artificial neural networks. It can mimic human brain mechanisms to observe and interpret various data, and combine low-level features to form high-level representations for attribute category prediction, thereby discovering deep features of the data. The training process of deep learning involves feature extraction and integration and large data acquisition and processing. Deep learning has become a research hotspot in the field of artificial intelligence in recent years due to its universality.

The function prediction of drugs (compounds) aims to predict new functions of known drugs or potential functions of compounds with unknown functions. The current drug development focuses on the design of compounds for disease targets. At present, there is another way to find small molecules that affect the expression profile of diseases, and establish a connection between small molecules and diseases through the correlation of the expression profile. This is called a connectivity map (CMAP) method, which does not rely on known disease targets. However, the existing CMAP technology is only applicable to 1,309 small molecule compounds with known data points, and cannot predict other molecules, especially virtual molecules.

SUMMARY OF THE INVENTION

Technical Problem: In order to overcome the shortcomings of the prior art, the present disclosure provides a gene expression variation prediction method based on a neural network.

Technical Solution: The present disclosure provides a compound function prediction method based on a neural network and a connectivity map (CMAP) algorithm. The compound function prediction method is used to predict an efficacy of a compound, and the compound function prediction method includes the following steps:

(1) acquiring a molecular formula of the compound from a public database; constructing a compound molecule-encoding vector neural network according to a molecular fingerprint generated based on a molecular structure or a molecular fingerprint acquired from another representation of the molecular structure; and training an autoencoder or a variational autoencoder based on the molecular formula of the compound for outputting an encoding vector of the compound molecule or outputting an encoding vector and an encoding radius vector of the compound molecule;

(2) acquiring compound-gene expression variation data from a public database; connecting a multi-layer deep learning network to the compound molecule-encoding vector neural network constructed in the step (1); and constructing and training an encoding vector-marker gene expression variation deep neural network for outputting a marker gene expression variation;

(3) acquiring marker gene expression level or gene expression variation-whole genome gene expression level or gene expression variation data from a public database; connecting a multi-layer deep learning network to the encoding vector-marker gene expression variation deep neural network constructed in the step (2); fitting with a linear equation or a nonlinear equation; constructing and training a marker gene expression level or gene expression variation-whole genome gene expression level or gene expression variation neural network; and calculating a linear or nonlinear relationship between a marker gene expression level or gene expression variation and a whole genome gene expression level or gene expression variation;

(4) acquiring a variation in a disease expression profile from a public database; defining upregulated and downregulated gene sets of a disease or a phenotype; and constructing, based on the compound molecule-encoding vector neural network, the encoding vector-marker gene expression variation deep neural network, the marker gene expression level or gene expression variation-whole genome gene expression level or gene expression variation neural network, and the upregulated and downregulated gene sets of the disease or the phenotype, a compound and disease or phenotype correlation evaluation system, including the compound molecule-encoding vector neural network, the encoding vector-marker gene expression variation deep neural network, the marker gene expression level or gene expression variation-whole genome gene expression level or gene expression variation neural network, and an evaluation system for a correlation between the whole genome gene expression level or gene expression variation corresponding to the compound and the upregulated and downregulated gene sets of the disease or the phenotype; and (5) inputting a molecular formula of a molecule to be evaluated into the compound and disease or phenotype correlation evaluation system to evaluate a correlation between the compound and the disease or the phenotype, specifically including, inputting the molecular formula of the molecule to be evaluated into the compound molecule-encoding vector neural network, and outputting an encoding vector; inputting the encoding vector into the encoding vector-marker gene expression variation deep neural network, and outputting the marker gene expression variation; inputting the marker gene expression variation into the marker gene expression level or gene expression variation-whole genome gene expression level or gene expression variation neural network, and outputting the whole genome gene expression level or gene expression variation; and inputting the whole genome gene expression level or gene expression variation and the upregulated and downregulated gene sets of the disease or the phenotype into the evaluation system for the correlation between the whole genome gene expression level or gene expression variation corresponding to the compound and the upregulated and downregulated gene sets of the disease or the phenotype, and outputting a score for a probability of the compound in treating or exacerbating the disease.

In the step (1), the public database includes but is not limited to PubChem, ensemble, and zinc; the molecular fingerprint includes but is not limited to an extended connectivity fingerprint, up to four bonds (ECFP4) and a morgan fingerprint; and the neural network includes but is not limited to an autoencoder, a variational autoencoder, a grammar variational autoencoder (GrammarVAE), a syntax-directed variational autoencoder (SDVAE), a junction tree variational autoencoder (Junction tree VAE), and a Transformer-based encoder.

In the step (2), the deep neural network includes a 1-finite multi-layer dense neural network, a 1-finite multi-layer dense neural network with a dropout layer or a control layer interspersed in any form; a non-fully connected neural network, a non-fully connected neural network with a dropout layer or a control layer interspersed in any form; and a neural network based on a probability weight but not in a form of a deep network; and any layer of the neural network is provided with an activation function, including but not limited to a linear activation function, a sigmoid activation function, a rectified linear unit (relu) activation function, and a tanh (hyperbolic tangent) activation function.

In the step (2), there are any number of marker genes, preferably 800-1,200, and more preferably around 1,000.

In the step (3), the public database includes but is not limited to gene expression omnibus (GEO) and arrayexpress; and marker gene-whole genome gene data is acquired through a technique including but not limited to microarray, ribonucleic acid sequencing (RNAseq), and L1000.

In the step (4), the public database includes but is not limited to GEO and arrayexpress; data of the upregulated and downregulated gene sets of the disease or the phenotype is acquired through a technique including but not limited to microarray, RNAseq, and single-cell RNAseq; and the correlation between the whole genome gene expression level or gene expression variation corresponding to the compound and the upregulated and downregulated gene sets of the disease or the phenotype is evaluated through a method including but not limited to a gene set enrichment analysis (GSEA) algorithm, an intersection method, a neural network method, and a machine learning method.

A function of the compound includes an activity and a side effect of the compound.

The activity of the compound includes but is not limited to anti-aging, treatment of hyperuricemia, weight loss, treatment of nonalcoholic steatohepatitis, fight against a novel coronavirus, and anti-oxidation.

The present disclosure further provides a compound and disease or phenotype correlation evaluation system based on a neural network and a connectivity map (CMAP) algorithm, including a compound molecule-encoding vector neural network, an encoding vector-marker gene expression variation deep neural network, a marker gene expression level-whole genome gene expression level deep neural network, and a correlation between a whole genome gene expression level or gene expression variation corresponding to a compound and upregulated and downregulated gene sets of a disease or a phenotype, and the compound and disease or phenotype correlation evaluation system is operated according to the following steps: inputting the molecular formula of the molecule to be evaluated into the compound molecule-encoding vector neural network, and outputting an encoding vector; inputting the encoding vector into the encoding vector-marker gene expression variation deep neural network, and outputting a marker gene expression variation; inputting the marker gene expression variation into the marker gene expression level or gene expression variation-whole genome gene expression level or gene expression variation neural network, and outputting the whole genome gene expression level or gene expression variation; and inputting the whole genome gene expression level or gene expression variation and the upregulated and downregulated gene sets of the disease or the phenotype into an evaluation system for the correlation between the whole genome gene expression level or gene expression variation corresponding to the compound and the upregulated and downregulated gene sets of the disease or the phenotype, and outputting a score for a probability of the compound in treating or exacerbating the disease.

Advantageous Effect: In the present disclosure, the compound function prediction method is proposed based on the neural network and the CMAP algorithm. The compound function prediction method can achieve high-throughput prediction of the correlation between the compound and the intracellular gene expression variation at the early stage of drug development, and can predict the compound's functions and long-term side effects according to the gene expression variation, greatly accelerating the process of drug development.

BRIEF DESCRIPTION OF THE DRAWINGS

FIG. 1 is a flowchart of calculation according to the present disclosure, where ① denotes a molecular formula of a compound; ② denotes a SMILES representation of the molecular formula of the compound; ③ denotes a syntax tree representation of the molecular formula; ④ denotes one-dimensional grammar encoding; ⑤ denotes that a one-dimensional grammar code is transformed into a one-hot code; ⑥ denotes a first layer of one-dimensional convolution with a length-9 convolutional kernel and there are a total of 9 independent filter matrices; ⑦ denotes a second layer of one-dimensional convolution with 9 independent filter matrices; ⑧ denotes a third layer of one-dimensional convolution with 10 independent filter matrices; ⑨ denotes flattening an output from a previous layer; ⑩ denotes a fully connected layer; ⑪ denotes a fully connected layer outputting a 56-dimensional core; ⑫ denotes a fully connected neural network outputting a 56-dimensional radius; ⑬ denotes that a coordinate vector of any point in a high-dimensional sphere is taken as a molecular encoding vector; ⑭ denotes a fully connected layer with a relu activation function; ⑮ denotes a dropout layer; ⑯ denotes a fully connected layer with a tanh activation function; ⑰ denotes a fully connected layer without any activation function, which is 978-dimensional, namely expression variations of 978 marker genes; ⑱ denotes a fully connected layer without any activation function, and outputting expression variations of 12,328 genes; ⑲ denotes upregulated and downregulated gene sets of the disease or the phenotype; and ⑳ denotes that a cell or animal experiment is conducted for a predicted result.

DETAILED DESCRIPTION OF THE EMBODIMENTS

The present disclosure is described in further detail below.

A method for predicting a function of an antioxidant compound based on a neural network and a connectivity map (CMAP) algorithm includes the following steps.

(1) A molecular formula of a compound is acquired from a public database, a compound molecule variational autoencoder (VAE) is constructed, and a VAE based on the molecular formula of the compound is trained, which outputs an encoding vector of the compound molecule.

Figure 1:
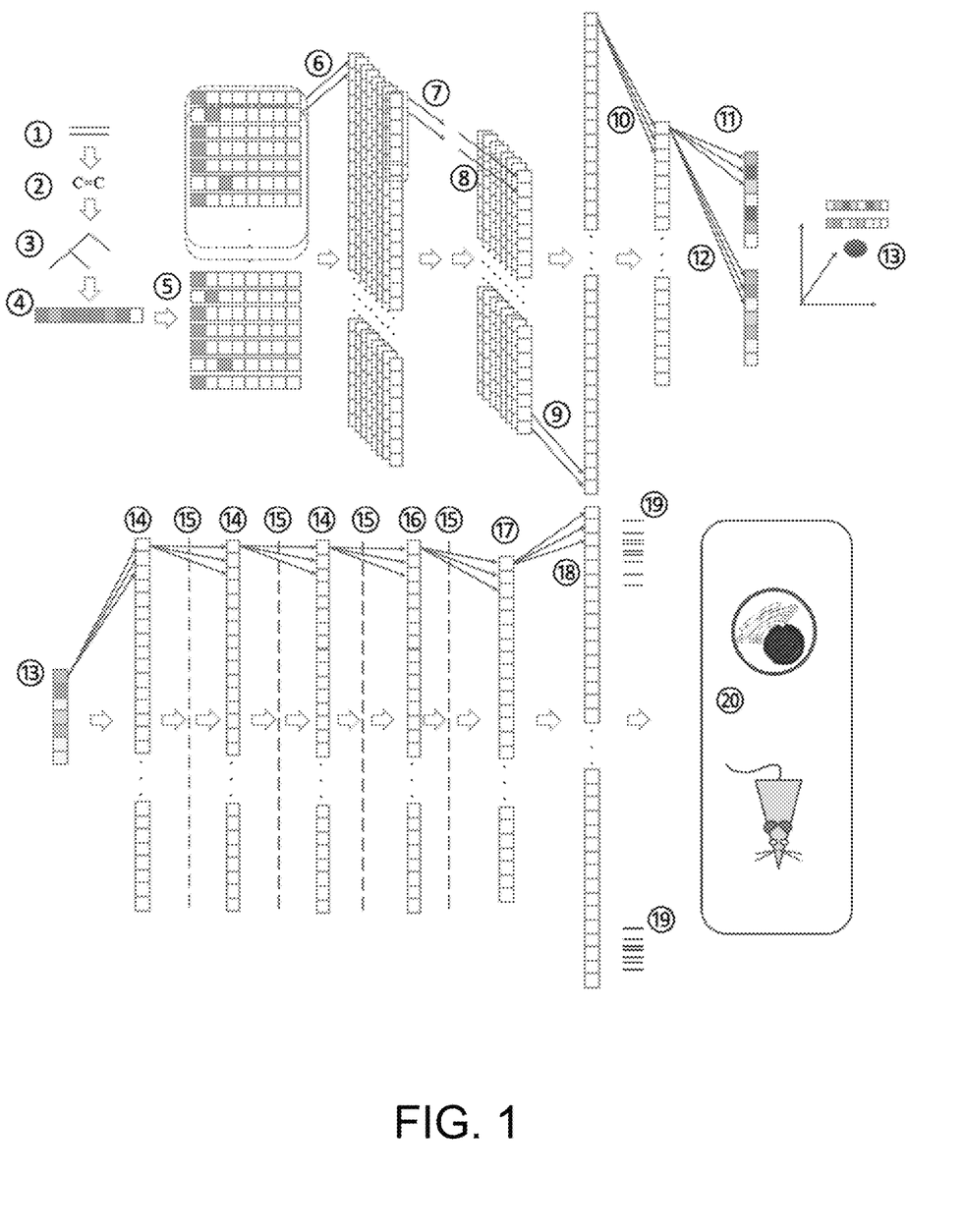

For example, the molecular formula of the compound is acquired from a public database such as PubChem, ensemble, and zinc. A compound molecule-encoding vector neural network is constructed according to a molecular structure, and a grammar VAE (GrammarVAE) based on the molecular formula of the compound is trained, as shown in FIG. 1, to output an encoding vector of the compound molecule.

Figure 2:
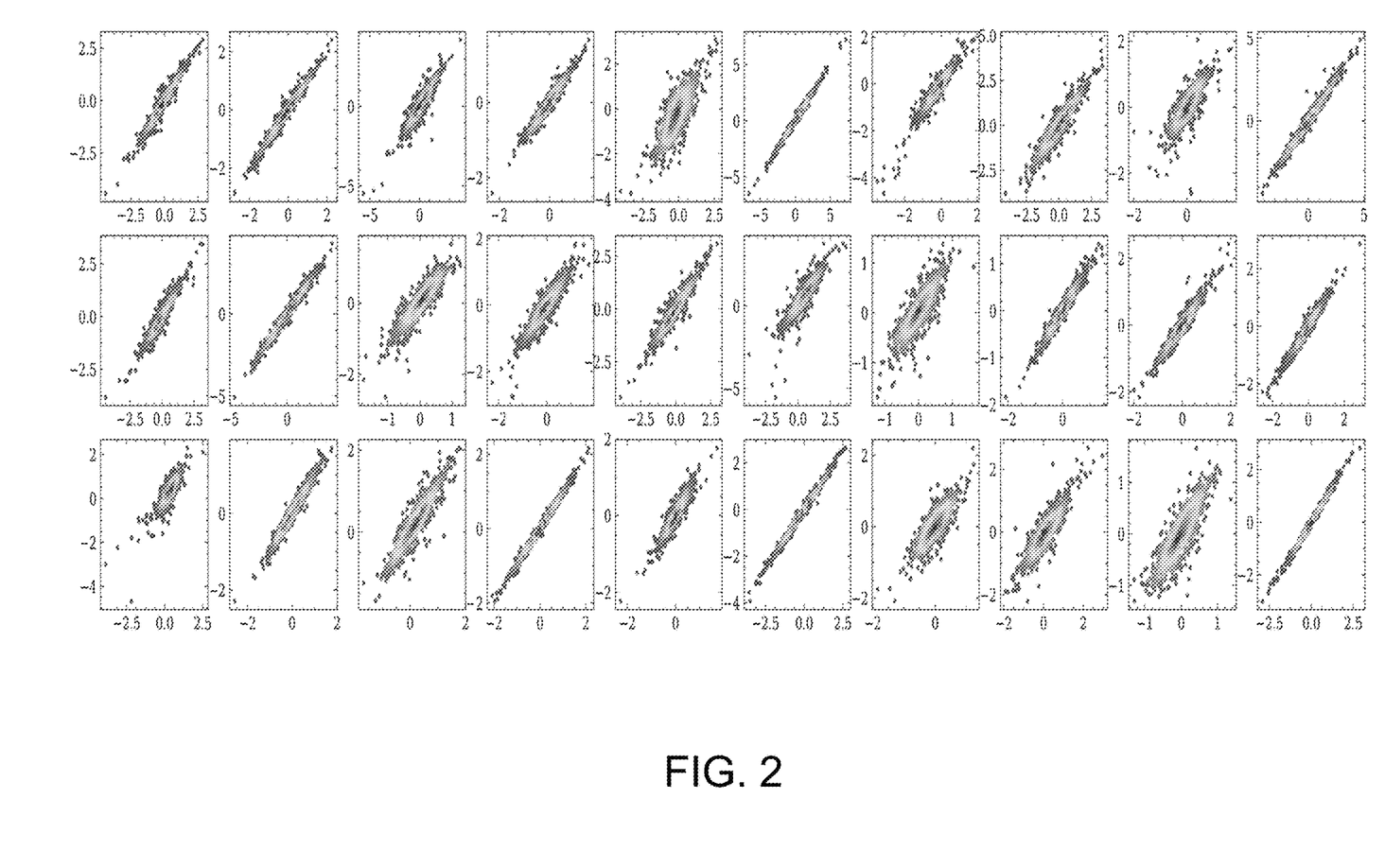
FIG. 2 is a scatter plot of predicted gene expression variations and experimentally measured gene expression variations of 978 marker genes in a training set.

(2) Compound-gene expression variation data is acquired from a public database such as CMAP, LINCS, and GEO. The compound molecule-encoding vector neural network constructed in the step (1) is connected to a 5-layer fully connected network (dense network). In the fully connected network, first four layers include 1,024 neurons, a fifth layer includes 978 neurons, first three layers are provided with a relu activation function, a fourth layer is provided with a tanh activation function, and the fifth layer is not provided with an activation function. Each layer is interspersed with a dropout layer, with a parameter of 0.25. An encoding vector-marker gene expression variation deep neural network is constructed and trained to output expression variations of marker genes, as shown in FIG. 2.

There are any number of marker genes, preferably 800-1,200, and more preferably around 1,000.

(3) Marker gene expression level or gene expression variation-whole genome gene expression level or gene expression variation data is acquired from a public database. The encoding vector-marker gene expression variation deep neural network constructed in the step (2) is connected to a 1-layer linear neural network. By training or mathematical calculation, a marker gene expression level-whole genome gene expression level transformation matrix is acquired, and a gene expression level-whole genome gene expression level transformation relationship is acquired.

The public database includes GEO and arrayexpress. Marker gene-whole genome gene data is acquired through a technique including microarray and RNAseq.

(4) White and brown fat gene expression profiles are acquired from a public database, and upregulated and downregulated gene sets of fat browning are calculated. Based on the compound molecule-encoding vector neural network, the encoding vector-marker gene expression variation deep neural network, the marker gene expression level-whole genome gene expression level deep neural network, and the upregulated and downregulated gene sets of the disease or the phenotype, a compound and disease or phenotype correlation evaluation system is constructed, including the compound molecule-encoding vector neural network, the encoding vector-marker gene expression variation deep neural network, and the marker gene expression level-whole genome gene expression level deep neural network, and the upregulated and downregulated gene sets of the disease or the phenotype.

The public database includes GEO, arrayexpress, or related literature. The upregulated and downregulated gene sets of fat browning are acquired through a technique including microarray.

A correlation between the compound and a disease or a phenotype is evaluated through a gene set enrichment analysis (GSEA) algorithm.

(5) A molecular formula of a molecule to be evaluated is input into the compound and disease or phenotype correlation evaluation system to evaluate a correlation between the compound and the disease or the phenotype. Specifically, the molecular formula of the molecule to be evaluated is input into the compound molecule-encoding vector neural network, and an encoding vector is output. The encoding vector is input into the encoding vector-marker gene expression variation deep neural network, and a marker gene expression variation is output. The marker gene expression variation is input into the marker gene expression variation-whole genome gene expression variation neural network, and a whole genome gene expression variation is output. An expression variation is calculated. The whole genome gene expression variation and the upregulated and downregulated gene sets for fat browning are input into the compound and disease or phenotype correlation evaluation system, and an effect size of the compound for promoting fat browning is scored. A scoring formula is as follows: Effect size:

$$a = \max_{j=1\,tot}\left[\frac{j}{t} - \frac{V(j)}{n}\right]$$

$$b = \max_{j=1\,tot}\left[\frac{j}{t} - \frac{V(j)}{n}\right]$$

$$\text{score} = \begin{cases} a-b & \text{when } b*a < 0 \\ 0 & \text{when } b*a > 0 \end{cases}$$

In the formula, t denotes a number of upregulated (or downregulated) genes; n denotes a total number of genes in a whole genome expression variation prediction system; and V(j) denotes a sequence number of a j-th upregulated (or downregulated) gene in descending order of variations among the n genes. To reverse a target gene set, it is necessary to multiply a score by −1 or take a plurality of molecules with a most negative score.

The present disclosure is described below according to a specific embodiment.

1. Based on an Existing Public Database, a Compound and Disease or Phenotype Correlation Evaluation System is Constructed, Including a Compound Molecule-Encoding Vector Neural Network, an Encoding Vector-Marker Gene Expression Variation Deep Neural Network, a Marker Gene Expression Variation-Whole Genome Gene Expression Variation Deep Neural Network, and Upregulated and Downregulated Gene Sets of a Disease or a Phenotype.

1.1 Compound Molecule-Encoding Vector Neural Network

The training data includes 25,0000 compound molecules, and the test data includes 30,000 compound molecules. SMILES encoding is performed, and it is transformed into a syntax tree. The syntax tree is traversed to generate a one-dimensional grammar code. A one-dimensional grammar code is transformed into a one-hot code. A length of 277 grammar nodes is taken as a maximum length, with each grammar node being 76-dimensional, representing a total of 76 different grammar nodes. A VAE is constructed, as shown in FIG. 1. In the VAE, first to third layers are one-dimensional convolutional neural networks with output dimensions of (269,9), (261,9), and (251,10), respectively. A fourth layer is a flattened layer with output dimensions of 2,510. A fifth layer is a fully connected layer with output dimensions of 435. A sixth layer is composed of two sub fully connected networks, which respectively output a coordinate vector and a standard deviation vector, both being 56-dimensional. This part forms an encoder part of the autoencoder. Sampling coordinates are generated with the coordinate vector as a center and the standard deviation vector as a radius. The sampling coordinates are input into a three-layer fully connected network to generate a one-hot code in form of SMILES. This part forms a decoder part of the autoencoder, and this part outputs a one-hot code for the SMILES syntax tree of the compound molecule, serving as an input into the encoder part. A loss function takes a Euclidean distance. The neural network is trained 30,000 times, and 512 molecules are randomly input each time. A success rate of generating molecules is monitored through the test data, and a proportion of identical molecules generated is 53%. A first half of the network is taken to generate a 56-dimensional code for generating an input for a next step.

1.2 Encoding Vector-Marker Gene Expression Variation Deep Neural Network

Figure 3:
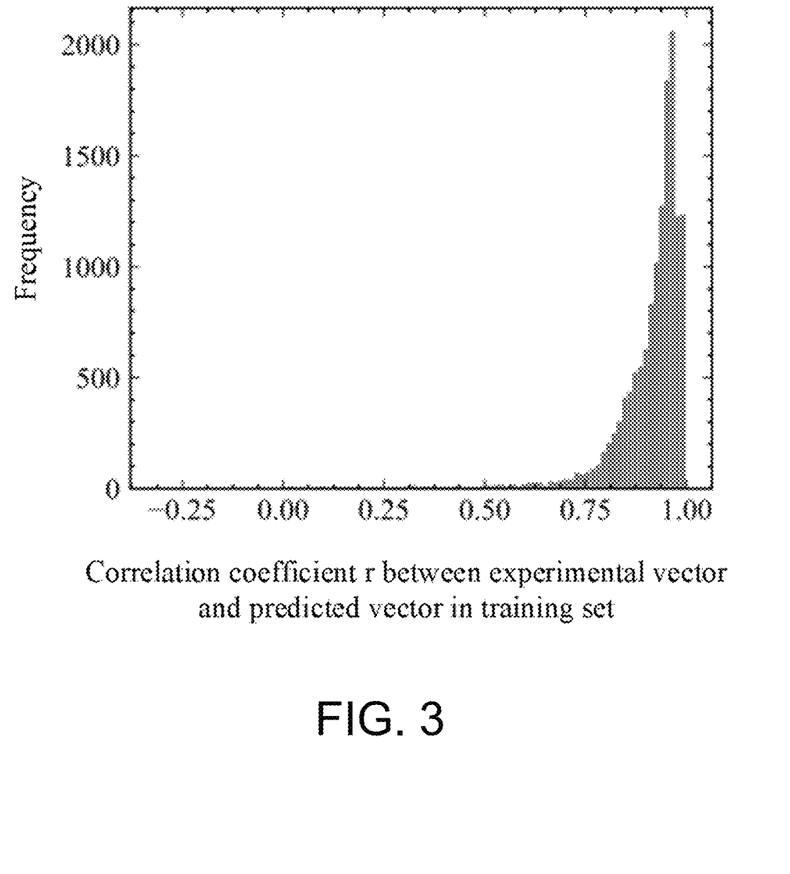
FIG. 3 is a probability distribution diagram of a correlation coefficient r between the predicted gene expression variations and the experimentally measured gene expression variations of the 978 marker genes in the training set.
Figure 4:
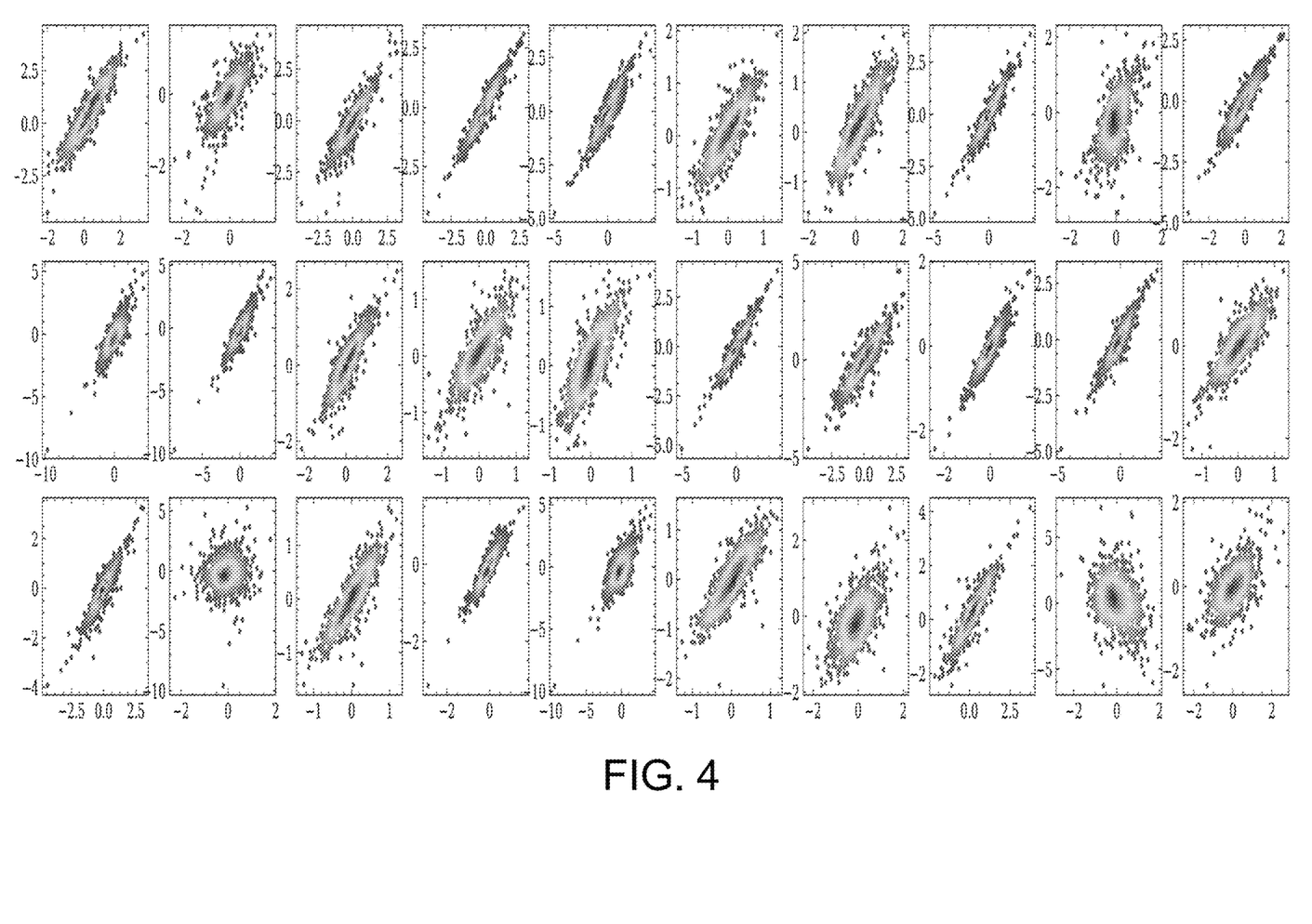
FIG. 4 is a scatter plot of predicted gene expression variations and experimentally measured gene expression variations of 978 marker genes in a test set.
Figure 5:
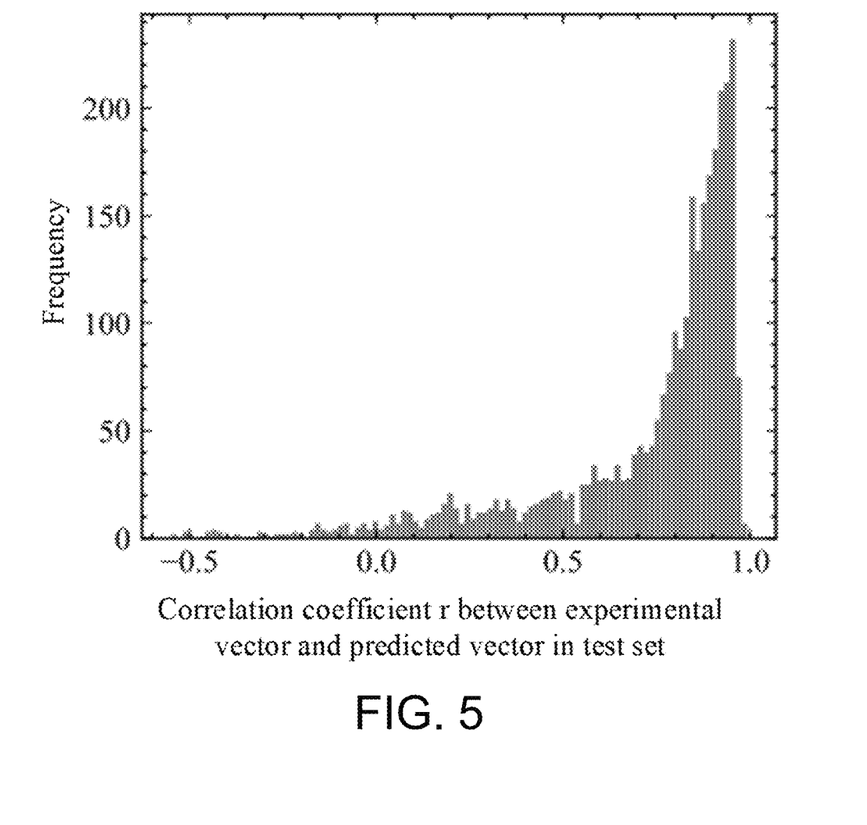
FIG. 5 is a probability distribution diagram of a correlation coefficient r between the predicted gene expression variations and the experimentally measured gene expression variations of the 978 marker genes in the test set.

Compound-gene expression variation data is acquired from a public database GEO (GSE92742). The compound molecule-encoding vector neural network constructed in the step (1) is connected to a 5-layer fully connected network (dense network). In the fully connected network, first four layers include 1,024 neurons, a fifth layer includes 978 neurons, first three layers are provided with a relu activation function, a fourth layer is provided with a tanh activation function, and the fifth layer is not provided with an activation function. Each layer is interspersed with a dropout layer, with a parameter of 0.25. An encoding vector-marker gene expression variation deep neural network is constructed and trained to output expression variations of marker genes, as shown in FIG. 2. A training set includes average expression variations of 14,051 compounds in all cell lines, and a test set includes average expression variations of 3,000 compounds in various cell lines. After training 30,000 times, a correlation evaluation value between a predicted expression profile variation in the training set and an experimental value is 0.90 (FIGS. 2 and 3). An average correlation between the predicted expression profile variation in the test set and an experimental value is 0.74 (FIGS. 4 and 5).

1.3 Marker Gene Expression Level-Whole Genome Gene Expression Level Neural Network A marker gene expression level-whole genome gene expression level single-layer neural network with 978 inputs and 12,328 outputs is constructed, without any activation function. 8,000 pieces of expression profile data are acquired from arrayexpress. 978 marker genes are taken from each piece of data as network inputs, and all genes are taken as outputs. 7,000 pieces of data are selected as the training set and 1,000 pieces of data as the test set. A correlation between the training set data and the test set data is 0.85. The transformation matrix can transform the expression variations of the 978 marker genes into the expression variations of the 12,328 genes.

1.4 Correlation Between Upregulated and Downregulated Gene Sets of the Disease or the Phenotype and Disease or Phenotype Taking novel coronavirus (SARS-CoV-2) as an example, the antiviral related genes include SLC1A5, CXADR, CAV2, NUP98, CTBP2, GSN, HSPA1B, STOM, RAB1B, HACD3, ITGB6, IST1, NUCKS1, TRIM27, APOE, SMARCB1, UBP1, CHMP1A, NUP160, HSPA8, DAG1, STAU1, ICAM1, CHMP5, DEK, VPS37B, EGFR, CCNK, PPIA, IFITM3, PPIB, TMPRSS2, and UBC, which form a set of genes to be upregulated in the system.

Taking nonalcoholic steatohepatitis as an example, a liver sample from a patient with nonalcoholic steatohepatitis III diagnosed clinically is taken for a transcriptome analysis.

The upregulated genes include GALC, CA3, ASRGL1, OR4K17, CCNG2, CCDC58, LUC7L2, FMC1-LUC7L2, AFTPH, MRPS21, ATM, SNX29, STX10, ENKD1, PLEKHO2, PAK4, ZNF330, TNPO3, RNASET2, PTPRJ, SNURF, SNRPN, F3, ATRIP, TREX1, EPM2AIP1, APAF1, CSRP1, SFXN5, FGFRL1, HSPA1L, and TIGD6. The downregulated genes include SLC9A3R2, OSBPL1A, C8G, HLA-G, ADGRF1, MAPK12, HDAC10, SNX29, DDX3X, VSTM4, PAQR3, RAD50, RAB11FIP2, PCGF5, CACNB2, and AP4S1. In order to search for a compound for treating the disease, compounds that can reverse the gene expression variations are predicted in the system and scored negative.

2. Evaluation on the Correlation Between Compound and Disease or Phenotype

The gene expression variation data in the step 1.3 is taken and sorted in descending order. Based on the gene fingerprint in the step 1.4, an ability of the compound molecule to fight against the novel coronavirus is scored by the GSEA algorithm.

3,680 compounds are tested, and 5 compounds with highest scores are acquired, including liquiritin, agnuside, procaterol, pibrentasvir, and carbocisteine.

The test verifies that liquiritin has a strong effect for fighting against the novel coronavirus, $EC_{50}$=2.39 uM. For specific data, please refer to Chinese patent application 202010309486.2 "Use of Liquiritin and Its Derivative in Preparation of Drug for Treating and/or Preventing Novel Coronavirus".

Taking nonalcoholic steatohepatitis as an example, compounds with high scores include trametinib, normilin, lupenone, telmisartan, bendroflumethiazide, and ravoxertinib. The test verifies that trametinib has a desired effect in the treatment of nonalcoholic steatohepatitis. For specific data, please refer to Chinese patent application 201911033194.4 "Use of Trimetinib in Preparation of Drug for Treating and/or Preventing Nonalcoholic Steatohepatitis and/or Nonalcoholic Fatty Liver Disease".

What is claimed is:

1. A compound function prediction method based on a neural network and a connectivity map algorithm, wherein the compound function prediction method is used to predict an efficacy of a compound, and the compound function prediction method comprising the following steps:
   (1) acquiring, by a processor, a molecular formula of the compound from a public database; constructing a compound molecule-encoding vector neural network according to a molecular fingerprint generated based on a molecular structure or a molecular fingerprint acquired from another representation of the molecular structure; and training an autoencoder or a variational autoencoder based on the molecular formula of the compound for outputting an encoding vector of the compound molecule or outputting an encoding vector and an encoding radius vector of the compound molecule;
   (2) acquiring, by the processor, compound-gene expression variation data from a public database; connecting a multi-layer deep learning network to the compound molecule-encoding vector neural network constructed in the step (1); and constructing and training an encoding vector-marker gene expression variation deep neural network for outputting a marker gene expression variation;
   (3) acquiring, by the processor, marker gene expression level or gene expression variation-whole genome gene expression level or gene expression variation data from a public database; connecting a multi-layer deep learning network to the encoding vector-marker gene expression variation deep neural network constructed in the step (2); fitting with a linear equation or a nonlinear equation; constructing and training a marker gene expression level or gene expression variation-whole genome gene expression level or gene expression variation neural network; and calculating a linear or nonlinear relationship between a marker gene expression level or gene expression variation and a whole genome gene expression level or gene expression variation;
   (4) acquiring, by the processor, a variation in a disease expression profile from a public database; defining upregulated and downregulated gene sets of a disease or a phenotype; and constructing, based on the compound molecule-encoding vector neural network, the encoding vector-marker gene expression variation deep neural network, the marker gene expression level or gene expression variation-whole genome gene expression level or gene expression variation neural network, and the upregulated and downregulated gene sets of the disease or the phenotype, a compound and disease or phenotype correlation evaluation system, comprising the compound molecule-encoding vector neural network, the encoding vector-marker gene expression variation deep neural network, the marker gene expression level or gene expression variation-whole genome gene expression level or gene expression variation neural network, and an evaluation system for a correlation between the whole genome gene expression level or gene expression variation corresponding to the compound and the upregulated and downregulated gene sets of the disease or the phenotype; and
   (5) inputting, by the processor, a molecular formula of a virtual molecule to be evaluated into the compound and disease or phenotype correlation evaluation system to evaluate a correlation between the compound and the disease or the phenotype, specifically comprising, inputting the molecular formula of the virtual molecule to be evaluated into the compound molecule-encoding vector neural network, and outputting an encoding vector; inputting the encoding vector into the encoding vector-marker gene expression variation deep neural network, and outputting the marker gene expression variation; inputting the marker gene expression variation into the marker gene expression level or gene expression variation-whole genome gene expression level or gene expression variation neural network, and outputting the whole genome gene expression level or gene expression variation; and inputting the whole genome gene expression level or gene expression variation and the upregulated and downregulated gene sets of the disease or the phenotype into the evaluation system for the correlation between the whole genome gene expression level or gene expression variation corresponding to the compound and the upregulated and downregulated gene sets of the disease or the phenotype, and outputting a score based on a scoring formula for a probability of the compound in treating or exacerbating the disease;
wherein the scoring formula is as follows:

$$a = \max_{j=1 \ to \ t} \left[ \frac{j}{t} - \frac{V(j)}{n} \right]$$

-continued $$b = \max_{j=1\,tot}\left[\frac{j}{t} - \frac{V(j)}{n}\right]$$

$$score = \begin{cases} a-b & \text{when } b*a < 0 \\ 0 & \text{when } b*a > 0 \end{cases}$$

wherein t denotes a number of upregulated (or downregulated) genes, n denotes a total number of genes in a whole genome expression variation prediction system, and V(j) denotes a sequence number of a j-th upregulated (or downregulated) gene in a descending order of gene expression variations among the n genes; and (6) screening out compounds capable of reversing the gene expression variations of the upregulated and downregulated gene sets of the disease or the phenotype based on the score, and filtering out a compound for treating the disease.

2. The compound function prediction method based on the neural network and the connectivity map algorithm according to claim 1, wherein in the step (1), the public database comprises but is not limited to PubChem, ensemble, and zinc; the molecular fingerprint comprises but is not limited to an extended connectivity fingerprint, up to four bonds (ECFP4) and a morgan fingerprint; and the neural network comprises but is not limited to an autoencoder, a variational autoencoder, a grammar variational autoencoder (Grammar-VAE), a syntax-directed variational autoencoder (SDVAE), a junction tree variational autoencoder (Junction tree VAE), and a Transformer-based encoder.

3. The compound function prediction method based on the neural network and the connectivity map algorithm according to claim 1, wherein in the step (2), the deep neural network comprises a 1-finite multi-layer dense neural network, a 1-finite multi-layer dense neural network with a dropout layer or a control layer interspersed in any form; a non-fully connected neural network, a non-fully connected neural network with a dropout layer or a control layer interspersed in any form; a neural network based on a probability weight but not in a form of a deep network; and any layer of the neural network is provided with an activation function, comprising but not limited to a linear activation function, a sigmoid activation function, a rectified linear unit (relu) activation function, and a tanh (hyperbolic tangent) activation function.

4. The compound function prediction method based on the neural network and the connectivity map algorithm according to claim 1, wherein in the step (2), there are any number of marker genes, preferably 800-1,200, and more preferably around 1,000.

5. The compound function prediction method based on the neural network and the connectivity map algorithm according to claim 1, wherein in the step (3), the public database comprises but is not limited to gene expression omnibus (GEO) and arrayexpress; and marker gene-whole genome gene data is acquired through a technique comprising but not limited to microarray, ribonucleic acid sequencing (RNAseq), and L1000.

6. The compound function prediction method based on the neural network and the connectivity map algorithm according to claim 1, wherein in the step (4), the public database comprises but is not limited to GEO and arrayexpress; data of the upregulated and downregulated gene sets of the disease or the phenotype is acquired through a technique comprising but not limited to microarray, RNAseq, and single-cell RNAseq; and the correlation between the whole genome gene expression level or gene expression variation corresponding to the compound and the upregulated and downregulated gene sets of the disease or the phenotype is evaluated through a method comprising but not limited to a gene set enrichment analysis (GSEA) algorithm, an intersection method, a neural network method, and a machine learning method.

7. The compound function prediction method based on the neural network and the connectivity map algorithm according to claim 1, wherein a function of the compound comprises an activity and a side effect of the compound.

8. The compound function prediction method based on the neural network and the connectivity map algorithm according to claim 1, wherein an activity of the compound comprises but is not limited to anti-aging, treatment of hyperuricemia, weight loss, treatment of nonalcoholic steatohepatitis, fight against a novel coronavirus, and anti-oxidation.

* * * * *